United States Patent
Soultanidis et al.

(10) Patent No.: US 9,790,139 B2
(45) Date of Patent: *Oct. 17, 2017

(54) PROCESS FOR CONVERTING OXYGENATES TO AROMATIC HYDROCARBONS

(71) Applicant: ExxonMobil Chemical Patents Inc., Baytown, TX (US)

(72) Inventors: Nikolaos Soultanidis, Houston, TX (US); Mayank Shekhar, Houston, TX (US); John S. Coleman, Fairfax, VA (US); Jeevan S. Abichandani, Houston, TX (US); Stephen J. McCarthy, Center Valley, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 184 days.

This patent is subject to a terminal disclaimer.

(21) Appl. No.: 14/560,953

(22) Filed: Dec. 4, 2014

(65) Prior Publication Data

US 2015/0175501 A1    Jun. 25, 2015

Related U.S. Application Data

(60) Provisional application No. 62/003,290, filed on May 27, 2014, provisional application No. 61/918,984, (Continued)

(30) Foreign Application Priority Data

Jul. 7, 2014    (EP) ..................................... 14176022

(51) Int. Cl.
*C07C 1/24* (2006.01)
*C07C 7/00* (2006.01)
(Continued)

(52) U.S. Cl.
CPC .................. *C07C 1/22* (2013.01); *C07C 1/24* (2013.01); *C07C 2/64* (2013.01); *C07C 5/2729* (2013.01);
(Continued)

(58) Field of Classification Search
None
See application file for complete search history.

(56) References Cited

U.S. PATENT DOCUMENTS 3,354,078 A    11/1967    Maile et al.
3,702,886 A    11/1972    Argauer et al.
(Continued)

FOREIGN PATENT DOCUMENTS

| CN | 101602643 | 12/2009 |
|---|---|---|
| CN | 101602648 | 12/2009 |

(Continued)

OTHER PUBLICATIONS

U.S. Appl. No. 14/560,889, filed Dec. 4, 2014, Ou et al.
(Continued)

*Primary Examiner* — Philip Louie (57) ABSTRACT

Processes for catalytically converting oxygenates to hydrocarbon products having an increased $C_6$-$C_8$ aromatics content therein. A first mixture comprising ≥10.0 wt. % of at least one oxygenate, based on the weight of the first mixture, contacts a catalyst in a fluidized bed reactor to produce a product stream including water, one or more hydrocarbons comprising ≥30.0 wt. % of aromatics, based on the weight of the hydrocarbons in the product stream, hydrogen, and one or more oxygenates. The catalyst comprises at least one molecular sieve, a binder, and at least one element selected from Groups 2-14 of the Periodic Table. At least one water-rich stream, at least one aromatic-rich hydrocarbon stream, and at least one aromatic-depleted hydrocarbon
(Continued)

stream are separated from the product stream, and at least a portion of one of the aromatic-rich hydrocarbon stream or the aromatic-depleted hydrocarbon stream is recycled back to the reactor.

26 Claims, 3 Drawing Sheets

Related U.S. Application Data filed on Dec. 20, 2013, provisional application No. 61/918,994, filed on Dec. 20, 2013, provisional application No. 61/919,013, filed on Dec. 20, 2013.

(51) Int. Cl.

| | | |
|---|---|---|
| *C07C 1/22* | (2006.01) | |
| *C07C 2/64* | (2006.01) | |
| *C07C 5/27* | (2006.01) | |
| *C07C 6/06* | (2006.01) | |
| *C07C 6/00* | (2006.01) | |
| *C10G 3/00* | (2006.01) | |
| *C10G 29/20* | (2006.01) | |

(52) U.S. Cl.
CPC ............... *C07C 6/00* (2013.01); *C07C 6/06* (2013.01); *C10G 3/49* (2013.01); *C10G 29/205* (2013.01); *C07C 2529/40* (2013.01); *C10G 2400/30* (2013.01); *Y02P 30/20* (2015.11); *Y02P 30/42* (2015.11)

(56) References Cited

U.S. PATENT DOCUMENTS

| | | | |
|---|---|---|---|
| 3,709,979 A | 1/1973 | Chu | |
| 3,760,024 A | 9/1973 | Cattanach | |
| 3,832,449 A | 8/1974 | Rosinski et al. | |
| 3,894,102 A | 7/1975 | Chang et al. | |
| 3,894,103 A | 7/1975 | Chang et al. | |
| 3,894,104 A | 7/1975 | Chang et al. | |
| 3,894,107 A | 7/1975 | Butter et al. | |
| 3,928,483 A | 12/1975 | Chang et al. | |
| 3,960,978 A | 6/1976 | Givens et al. | |
| 4,016,218 A | 4/1977 | Haag et al. | |
| 4,016,245 A | 4/1977 | Plank et al. | |
| 4,021,502 A | 5/1977 | Plank et al. | |
| 4,025,571 A | 5/1977 | Lago | |
| 4,035,430 A | 7/1977 | Dwyer et al. | |
| 4,046,685 A | 9/1977 | Bray | |
| 4,049,573 A | 9/1977 | Kaeding | |
| 4,058,576 A | 11/1977 | Chang et al. | |
| 4,076,842 A | 2/1978 | Plank et al. | |
| 4,079,095 A | 3/1978 | Givens et al. | |
| 4,088,706 A | 5/1978 | Kaeding | |
| RE29,948 E | 3/1979 | Dwyer et al. | |
| 4,150,062 A | 4/1979 | Garwood et al. | |
| 4,157,293 A | 6/1979 | Plank et al. | |
| 4,211,640 A | 7/1980 | Garwood et al. | |
| 4,227,992 A | 10/1980 | Garwood et al. | |
| 4,288,645 A | 9/1981 | Wagstaff | |
| 4,291,182 A | 9/1981 | Dautzenberg et al. | |
| 4,326,994 A | 4/1982 | Haag et al. | |
| 4,397,827 A | 8/1983 | Chu | |
| 4,403,044 A | 9/1983 | Post et al. | |
| 4,417,780 A | 11/1983 | Knapp | |
| 4,423,274 A | 12/1983 | Daviduk et al. | |
| 4,433,185 A | 2/1984 | Tabak | |
| 4,433,189 A | 2/1984 | Young | |
| 4,450,311 A | 5/1984 | Wright et al. | |
| 4,456,779 A | 6/1984 | Owen et al. | |
| 4,538,017 A | 8/1985 | Butler et al. | |
| 4,556,477 A | 12/1985 | Dwyer | |
| 4,579,993 A | 4/1986 | Bowes et al. | |
| 4,582,815 A | 4/1986 | Bowes | |
| 4,584,423 A | 4/1986 | Nacamuli et al. | |
| 4,590,321 A | 5/1986 | Chu | |
| 4,621,161 A | 11/1986 | Shihabi | |
| 4,628,135 A | 12/1986 | Owen et al. | |
| 4,665,251 A | 5/1987 | Chu | |
| 4,720,602 A | 1/1988 | Chu | |
| 4,788,369 A | 11/1988 | Marsh et al. | |
| 4,808,763 A | 2/1989 | Shum | |
| 5,365,004 A | 11/1994 | Beck et al. | |
| 5,367,099 A | 11/1994 | Beck et al. | |
| 5,625,103 A | 4/1997 | Abichandani et al. | |
| 5,633,417 A | 5/1997 | Beck et al. | |
| 5,675,047 A | 10/1997 | Beck et al. | |
| 5,705,726 A | 1/1998 | Abichandani et al. | |
| 5,877,368 A | 3/1999 | Kiyama et al. | |
| 5,883,034 A | 3/1999 | Drake et al. | |
| 5,998,688 A | 12/1999 | Abichandani et al. | |
| 6,028,238 A | 2/2000 | Beck et al. | |
| 6,048,815 A | 4/2000 | Yao et al. | |
| 6,156,689 A | 12/2000 | Kimble et al. | |
| 6,177,374 B1 | 1/2001 | Pradhan et al. | |
| 6,187,982 B1 | 2/2001 | Beck et al. | |
| 6,372,680 B1 | 4/2002 | Wu et al. | |
| 6,372,949 B1 | 4/2002 | Brown et al. | |
| 6,417,421 B1 | 7/2002 | Yao | |
| 6,423,879 B1 | 7/2002 | Brown et al. | |
| 6,504,072 B1 | 1/2003 | Brown et al. | |
| 6,506,954 B1 * | 1/2003 | Brown | C07C 1/20 585/469 |
| 7,285,511 B2 | 10/2007 | Ghosh et al. | |
| 7,304,194 B2 | 12/2007 | Ghosh et al. | |
| 7,453,018 B2 | 11/2008 | Dakka et al. | |
| 7,722,825 B1 | 5/2010 | Bozzano et al. | |
| 7,799,962 B2 | 9/2010 | Dakka et al. | |
| 2006/0161035 A1 | 7/2006 | Kalnes et al. | |
| 2009/0124841 A1 * | 5/2009 | Rothaemel | B01D 3/143 585/639 |
| 2013/0123557 A1 | 5/2013 | McCarthy et al. | |
| 2013/0158323 A1 | 6/2013 | Mondal | |
| 2013/0165725 A1 | 6/2013 | Chewter et al. | |
| 2013/0281753 A1 | 10/2013 | McCarthy et al. | |
| 2013/0303814 A1 | 11/2013 | Mammadov et al. | |
| 2014/0018592 A1 | 1/2014 | Chen et al. | |

FOREIGN PATENT DOCUMENTS

| | | |
|---|---|---|
| CN | 101607864 | 12/2009 |
| CN | 101780417 | 7/2010 |
| CN | 101823929 | 9/2010 |
| EP | 0 123 449 | 10/1984 |
| EP | 0 172 686 | 2/1986 |
| WO | WO 99/51549 | 10/1999 |
| WO | WO 01/29152 | 4/2001 |
| WO | WO 2005/068406 | 7/2005 |
| WO | WO 2006/012150 | 2/2006 |
| WO | 2009/021726 | 2/2009 |
| WO | WO 2009/021726 | 2/2009 |
| WO | WO 2013/017497 | 2/2013 |

OTHER PUBLICATIONS

U.S. Appl. No. 62/003,290, filed May 27, 2014, Ou et al.
U.S. Appl. No. 61/918,984, filed Dec. 20, 2013, McCarthy et al.
U.S. Appl. No. 61/918,994, filed Dec. 20, 2013, McCarthy et al.
U.S. Appl. No. 61/919,013, filed Dec. 20, 2013, McCarthy et al.
U.S. Appl. No. 62/057,855, filed Sep. 30, 2014, Buchanan et al.
Chang et al., "The Conversion of Methanol and Other O-Compounds to Hydrocarbons over Zeolite Catalysts," Journal of Catalysis, vol. 47 (1977), pp. 249-259.
Ono et al., "*Selective Conversion of Methanol into Aromatic Hydrocarbons over Zinc-exchanged ZSM-5 Zeolites,*" Journal of the Chemical Society, Faraday Transactions 1, vol. 84, No. 4, Jan. 1988, p. 1091-1099.
Inoue et al., "*Selective conversion of methanol into aromatic hydrocarbons over silver-exchanged ZSM-5 zeolites,*" Microporous Materials, vol. 4, No. 5, Aug. 1995, pp. 379-383.

(56) References Cited

OTHER PUBLICATIONS

Woltermann et al., "*Chapter 4 Commercial Preparation and Characterization of FCC Catalysts*", Studies in Surface Science and Catalysis, 1993, vol. 76, pp. 105-144.
Eastwood et al., "*Thermofor Catalytic Cracking Unit*", Industrial and Engineering Chemistry, Dec. 1947, vol. 39, No. 12, pp. 1685-1690.
Yoshio Ono et al. "Selective conversion of methanol into aromatic hydrocarbons over zinc-exchanged ZSM-5 zeolites", Journal of the Chemical Society, Faraday Transactions 1, vol. 84, No. 4, Jan. 1988(Jan. 1988).
Yoshihiro Inoue et al., "Selective conversion of methanol into aromatic hydrocarbons over silver-exchanged ZSM-5 zeolites", Microporous Materials, vol. 4, No. 5, Aug. 1995 (Aug. 1995).

\* cited by examiner

PROCESS FOR CONVERTING OXYGENATES TO AROMATIC HYDROCARBONS

CROSS REFERENCE TO RELATED APPLICATIONS

This application claims priority to Provisional U.S. Patent Application Ser. No. 62/003,290, filed May 27, 2014; Provisional U.S. Patent Application Ser. No. 61/918,984 filed Dec. 20, 2013; Provisional U.S. Patent Application Ser. No. 61/918,994 filed Dec. 20, 2013; Provisional U.S. Patent Application Ser. No. 61/919,013 filed Dec. 20, 2013; and EP 14176022.3 filed Jul. 7, 2014, the disclosures of which are incorporated herein by reference in their entireties.

FIELD OF THE INVENTION

The present invention relates to processes for converting oxygenates to aromatic hydrocarbons. In particular, embodiments of the invention related to the conversion of methanol to $C_6$-$C_8$ aromatic hydrocarbons, particularly para-xylene.

BACKGROUND OF THE INVENTION

Aromatic hydrocarbons, such as benzene, toluene, xylene, etc., are useful as fuels, solvents, and as feeds for various chemical processes. Of the aromatics, those having 6 to 8 carbon atoms (e.g., benzene, toluene, and xylene) are especially desired. Para-xylene ("p-xylene") is particularly useful for manufacturing phthalic acids such as terephthalic acid, which is an intermediate in the manufacture of synthetic fibers such as polyester fibers.

One conventional process for producing aromatics involves reacting an oxygenate, such as methanol, in the presence of zeolite, such as ZSM-5, to produce water and a hydrocarbon product containing aromatics. See, e.g., C. D. Chang and A. J. Silvestri, *Journal of Catalysis* 47, p. 249 (1977), which discloses a process featuring high methanol conversion in approximately stoichiometric yield to produce about 44 wt. % hydrocarbon and about 56 wt. % of water, based on total product weight. Water and a portion of the hydrocarbon are condensed by exposing the product to a temperature <100° C., with the vapor being recycled to the reactor inlet. The vapor, which comprises about 20 wt. % of the hydrocarbon product, contains primarily $C_1$-$C_4$ paraffin and $C_2$-$C_4$ olefin. At a reaction temperature of about 370° C. and a liquid hourly space velocity (LHSV) of approximately 1.0 hr$^{-1}$, approximately 80 wt. % of the hydrocarbon product comprises gasoline boiling-range hydrocarbons, including $C_6$-$C_{11}$ aromatics. Under these conditions, the hydrocarbon product comprises approximately 30 wt. % of $C_6$-$C_8$ aromatics and approximately 10 wt. % of $C_{9+}$ hydrocarbon, primarily 1,2,4,5-tetramethylbenzene (i.e., durene). Durene can be removed by selectively hydrotreating the aromatic portion of the hydrocarbon product.

It is desired to convert oxygenates to hydrocarbons with an increase in the relative amount of $C_6$-$C_8$ aromatics in the hydrocarbon product as the $C_6$-$C_8$ aromatics are commercially useful. It is particularly desired to do so without increasing (i) the relative amount of durene in the aromatic portion of the hydrocarbon product to avoid extensively treating the product to remove durene toxic and/or (ii) the rate of catalyst deactivation. It is even more desired to do this while increasing the relative amount of p-xylene in the hydrocarbon product since p-xylene is the most commercially desired of the $C_6$-$C_8$ aromatics.

SUMMARY OF THE INVENTION

It has been found that oxygenates can be catalytically converted to hydrocarbon products having an increased $C_6$-$C_8$ aromatics content in the hydrocarbon product compared to conventional processes. The process utilizes a catalyst comprising (i) ≥10.0 wt. % of at least one molecular sieve and (ii) ≥0.1 wt. % of at least one element selected from Groups 2-14 of the Periodic Table. The invention is based in part on the discovery that utilizing one or more elements from Groups 2-14 of the Periodic Table provides the catalyst with a dehydrogenation functionality that surprisingly produces molecular hydrogen and an increased aromatics yield, but without producing a significant amount of carbon monoxide and carbon dioxide.

It has also been found that recycling and combining at least a portion of the aromatics in the hydrocarbon product with the oxygenate unexpectedly leads to one or more of the following advantages. In particular embodiments, recycling and combining at least a portion of the aromatics in the hydrocarbon product provides an increase in the relative amount of aromatics in the hydrocarbon product. The increase in aromatics may be achieved without a significant increase in the rate of catalyst deactivation and/or without a significant increase in the relative amount of durene in the aromatic portion of the hydrocarbon product. Advantageously and contrary to expectations, recycling and combining with the oxygenate at least a portion of the aromatics in the hydrocarbon product does not suppress methanol conversion to aromatic products. Under particular conditions, recycling of the aromatics can actually provide an overall increase in product aromatics content. Surprisingly, the catalyst may not experience a significant increase in deactivation rate, e.g., from over-reacting the recycled aromatics, even at elevated reaction temperatures (e.g., end of run conditions). And under certain conditions, the relative amount of durene in the aromatic portion of the product may not increase, even though recycling of xylenes to a chemical environment rich in CH2 fragments would be expected to result in alkylation to $C_{9+}$ aromatics. At least a portion of the olefins and paraffins in the hydrocarbon product may be recycled as well, leading to further conversion of the olefins and paraffins to aromatics without causing a significant increase in catalyst deactivation.

The process can be operated continuously in a fluidized or moving bed reactor such that the catalyst may be continuously regenerated, allowing a higher operating temperature and thereby yielding an increase in the amount of aromatics produced.

DETAILED DESCRIPTION

The present process is useful for the conversion a first mixture comprising oxygen-containing organic compounds (i.e., "oxygenates") into hydrocarbon products where the conversion is carried out by an exothermic catalytic reaction. Surprisingly, recycling at least a portion of the aromatics, olefins, or paraffins in the product with the oxygenate increases the yield of aromatics under particular conditions. Further, conducting such process in a fluidized or moving bed reactor, as opposed to a fixed bed reactor, allows for the use of higher temperatures, leading to higher conversion to aromatics.

As used herein, the phrase "at least a portion of" means >0 to 100.0 wt % of the process stream or composition to which the phrase refers.

As used herein, the term "first mixture" means a hydrocarbon-containing composition including one or more oxygenates. Typically, the first mixture comprises ≥10.0 wt % of at least one oxygenate, based on the weight of the first mixture, preferably ≥about 50.0 wt %, more preferably ≥about 90.0 wt %, and most preferably ≥about 99.0 wt %. Ranges expressly disclosed include combinations of any of the above-enumerated values; e.g., ≥10.0 to about 100.0 wt %, about 12.5 to about 99.5 wt %, about 20.0 to about 90.0, about 50.0 to about 99.0 wt %, etc.

As used herein, the term "oxygenate," "oxygenate composition," and the like refer to oxygen-containing compounds having 1 to about 20 carbon atoms, preferably 1 to about 10 carbon atoms, more preferably 1 to about 8 carbon atoms, and most preferably 1 to about 5 carbon atoms. Exemplary oxygenates include alcohols, ethers, carbonyl compounds, e.g., aldehydes, ketones and carboxylic acids, and mixtures thereof. Particular oxygenates methanol, ethanol, dimethyl ether, diethyl ether, methylethyl ether, diisopropyl ether, dimethyl carbonate, dimethyl ketone, formaldehyde, and acetic acid.

In any aspect, the oxygenate comprises one or more alcohols, preferably alcohols having 1 to about 10 carbon atoms, more preferably 1 to about 8 carbon atoms, or most preferably 1 to about 6 carbon atoms. The alcohols useful as first mixtures may be linear or branched, substituted or unsubstituted aliphatic alcohols and their unsaturated counterparts. Non-limiting examples of such alcohols include methanol, ethanol, propanols (e.g., n-propanol, isopropanol), butanols (e.g., n-butanol, sec-butanol, tert-butyl alcohol), pentanols, hexanols, etc., and mixtures thereof. In any aspect described herein, the first mixture may be one or more of methanol, and/or ethanol, particularly methanol. In any aspect, the first mixture may be methanol and dimethyl ether.

The oxygenate, particularly where the oxygenate comprises an alcohol (e.g., methanol), may optionally be subjected to dehydration, e.g., catalytic dehydration over γ-alumina Typically, such catalytic dehydration decreases the amount of water in the oxygenate by converting a portion of the water and alcohol to an ether, e.g., dimethyl ether (DME), in the first mixture and also allows partial heat recovery. Further optionally, at least a portion of any methanol and/or water remaining in the first mixture after catalytic dehydration may be separated from the first mixture.

In any aspect, one or more other compounds may be present in first mixture. Typically, although not necessarily, such compounds include one or more heteroatoms other than oxygen. Some such compounds include amines, halides, mercaptans, sulfides, and the like. Particular such compounds include alkyl-mercaptans (e.g., methyl mercaptan and ethyl mercaptan), alkyl-sulfides (e.g., methyl sulfide), alkyl-amines (e.g., methyl amine), and alkyl-halides (e.g., methyl chloride and ethyl chloride). In any aspect, the first mixture includes one or more of ≥1.0 wt % acetylene, pyrolysis oil or aromatics, particularly $C_6$ and/or $C_7$ aromatics.

The catalyst used herein is a composition of matter comprising a molecular sieve and a Group 2-14 element of the Periodic Table. In this sense, the term "comprising" can also mean that the catalyst can comprise the physical or chemical reaction product of the molecular sieve and the Group 2-14 element. Optionally, the catalyst may also include a filler or binder and may be combined with a carrier to form slurry.

For the purposes of this description and claims, reference to a group number for an element corresponds to the current IUPAC numbering scheme for the periodic table. Therefore, a "Group 4 metal" is an element from Group 4 of the Periodic Table, e.g., Hf, Ti, or Zr. The more preferred molecular sieves are SAPO molecular sieves, and metal-substituted SAPO molecular sieves. In particular embodiments, one or more Group 2 elements (e.g., Be, Mg, Ca, Sr, Ba, and Ra) may be used. In other embodiments, one or more Group 3 elements (e.g., Sc and Y), a Lanthanide (e.g., La, Ce, Pr, Nd, Sm, Eu, Gd, Tb, Dy, Ho, Er, Tm, Yb, and Lu), and/or an Actinide may be used. Catalysts comprising at least one Group 4 transition metal (e.g., Ti, Zr, and Hf) may be particularly useful. Likewise, some catalysts may benefit from the presence of at least one Group 5 and/or Group 6 element (e.g., V, Nb, Ta, Cr, Mo, and W). One or more Group 7-9 element (e.g., Mn, Tc, Re, Fe, Ru, Os, Co, Rh, and Ir) may also be used. In some embodiments, the Group 2-14 element comprises one or more Group 11 and/or Group 12 elements (e.g., Cu, Ag, Au, Zn, and Cd) may be used. In still other embodiments, one or more Group 13 elements (B, Al, Ga, In, and Tl). In a preferred embodiment, the metal is selected from the group consisting of Zn, Cd, Ag, and Cu, ideally Zn.

The molecular sieve comprises ≥10.0 wt. % of the catalyst, preferably about 40 to 100 wt. %, more preferably about 60 to 100 wt. %, and most preferably about 80 to 100 wt. %, the weight percent excluding any binder that may be used. As used herein the term "molecular sieve" refers to crystalline or non-crystalline materials having a porous structure. Microporous molecular sieves typically have pores having a diameter of ≤about 2.0 nm. Mesoporous molecular sieves typically have pores with diameters of about 2 to about 50 nm. Macroporous molecular sieves have pore diameters of >50.0 nm. The pore diameter of the molecular sieve used is preferably about 0.1 to 50 nm, more preferably 0.1 to 25 nm, and most preferably 0.1 to 10 nm.

Additionally or alternatively, some molecular sieves useful herein are described by a Constraint Index of about 1 to about 12. Constraint Index is determined as described in U.S. Pat. No. 4,016,218, incorporated herein by reference for details of the method.

Particular molecular sieves are zeolitic materials. Zeolitic materials are crystalline or para-crystalline materials. Some zeolites are aluminosilicates comprising [SiO$_4$] and [AlO$_4$] units. Other zeolites are aluminophosphates (AlPO) having structures comprising [AlO$_4$] and [PO$_4$] units. Still other zeolites are silicoaluminophosphates (SAPO) comprising [SiO$_4$], [AlO$_4$], and [PO$_4$] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 10 to 100, preferably about 10 to 80, more preferably about 20 to 60, and most preferably about 20 to 40.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZK5, erionite, and chabazite.

The catalyst also includes at least one element selected from Groups 2-14 of the Periodic Table. Typically, the total weight of the Group 2-14 elements is ≥0.1 wt. % and ≤about 20.0 wt. %, preferably about 1 to 20.0 wt. %, more preferably about 1 to 10.0 wt. %, and most preferably about 1 to 5 wt. %. %, the weight percent excluding any binder that may be used. Of course, the total weight of the Group 2-14 elements shall not include amounts attributable to the molecular sieve itself or any binder that is used.

Particular molecular sieves and Group 2-14-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ElAPSO where El is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, *Handbook of Molecular Sieves*, Van Nostrand Reinhold, New York, N.Y. (1992), which is herein fully incorporated by reference.

In one embodiment, the molecular sieve as modified by the Group 2-14 element is a ZSM-5 based molecular sieve and the Group 2-14, element is selected from elements of Groups 11-12, particularly Zn.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

The catalyst employed in the present process preferably includes a binder or matrix materials that are mechanically robust, minimize attrition of the bound catalyst, resistant to the temperatures and other conditions employed in the process in addition to the materials previously discussed. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. Examples of binders suitable for the catalyst are described in U.S Patent Publication Nos. 2014/0217940, 2014/0066675, 2014/0100402, and U.S. application Ser. No. 14/153,399, each of which is incorporated herein by reference.

Naturally occurring clays which can be utilized in the present catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. It will be recognized that the specific clay used and treatment thereof will affect performance to some extent, and the determination of the most appropriate clay (or binder more generally) is within the skill of the ordinary artisan in possession of the present disclosure to determine by routine experimentation.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

Generally, the catalyst will contain from preferably about 1 to 90.0 wt. %, more preferably about 30.0 to 90.0 wt. %, and most preferably about 50.0 to 90.0 wt. % of binder, ascertainable by one skilled in the art dependent upon the reactor configuration used.

Figure 1:
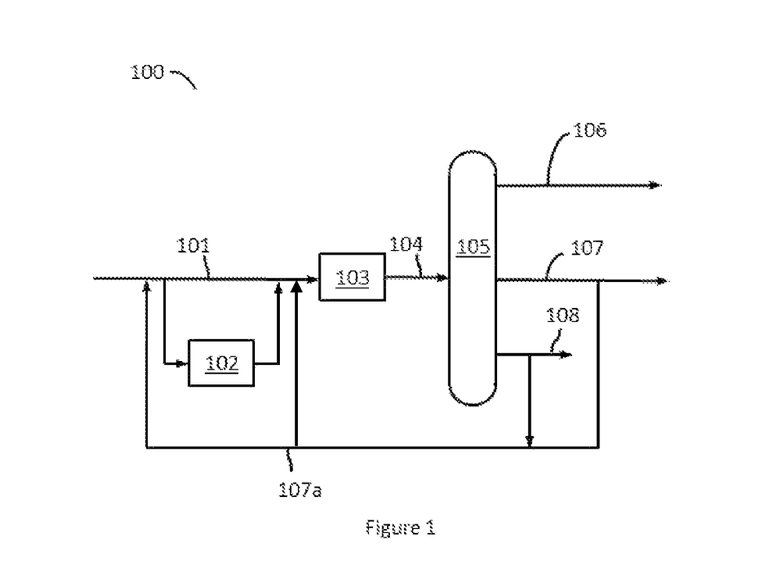
FIG. 1 illustrates a process according to an embodiment of the invention.

A process for converting an oxygenate-containing first mixture to a hydrocarbon stream containing aromatic molecules in the present of the catalyst described above will now be described. FIG. 1 schematically illustrates a process 100 wherein an oxygenated-containing feed is provided via line 101 to a reactor 103 and/or, optionally, to an optional dehydration unit 102 and then to a reactor 103. Reactor 103 may be any reactor suitable for converting an oxygenate-containing first mixture to an aromatics-containing hydrocarbon effluent. In a preferred embodiment, the reactor 103 is a fluidized or moving bed reactor system having the catalyst therein.

A fluidized or moving bed reactor system generally comprises a reactor and a catalyst regenerator. Air is introduced into the reactor to fluidize the catalyst particles and form a fluid bed. A feed comprising reactants enters the fluid bed reactor via a conduit and reacts with the fluidized catalyst. The catalyst circulates between the reactor and catalyst regenerator via conduits, and may pass through an apparatus which strips fluid from the catalyst. The partially deactivated catalyst is oxidatively regenerated by controlled contact with air or other regeneration gas at elevated temperature in the catalyst regenerator to remove carbonaceous deposits and restore acid activity. Regenerated catalyst is then transferred back to the reactor. A series of sequentially connected cyclone separators may be provided with dip legs to return any entrained catalyst fines to the fluid bed. These separators are positioned in an upper portion of the reactor. The product effluent separated from catalyst particles in the cyclone separating system is then withdrawn from the reactor. The recovered hydrocarbon product comprising aromatics, including para-xylene, is thereafter processed as required to separate the desired para-xylene from other reaction products or unconverted feed. Because the catalyst is continuously regenerated, the reactor may be operated at a higher temperature, leading to a higher conversion to aromatics.

Reactor 103 is operated under conditions to produce a product stream comprising water, one or more hydrocarbons, hydrogen, and one or more oxygenates, wherein said one or more hydrocarbons comprise ≥30.0 wt. % of aromatics, based on the weight of said one or more hydrocarbons in the product stream. In particular embodiments, the amount of aromatics in the hydrocarbon may be preferably about 30.0 to 90.0 wt. %, more preferably about 40.0 to 90.0 wt. %, and most preferably about 60.0 to 90 wt. %.

In particular embodiments, the aromatics comprise ≥10.0 wt. % paraxylene based on the weight of the aromatics, preferably about 1 to 50 wt. %, more preferably about 5 to 50 wt. %, and most preferably about 10 to 50 wt. %.

In particular embodiments, the hydrocarbons of the product stream comprises ≥80.0 wt. % of aromatics, based on the weight of the hydrocarbon, and ≤30.0 wt. % of the aromatics comprise durene, based on the weight of the aromatics. In particular embodiments, the amount of aromatics in the hydrocarbon of the product stream may be about 80.0 to 100.0 wt. %, preferably about 90.0 to 100.0 wt. %, and most preferably about 95.0 to 100.0 wt. %; and the amount of durene in the aromatics comprises about 0.1 to 30.0 wt. %, preferably 0.1 to 20.0 wt. %, and more preferably about 0.1 to 10.0 wt. %.

One of the products in the product stream exiting reactor 103 is hydrogen. Preferably hydrogen is present in an amount ≥0.05 wt. %, preferably about 0.1 to 5 wt. %, more preferably about 2 to 5 wt. %, and most preferably about 3 to 5 wt. %.

In particular embodiments, the product stream from reactor 103 comprises ≤3.0 wt. % carbon monoxide, the weight percent of carbon monoxide being based on the total weight of the product stream. Exemplary amounts of carbon monoxide include about 0.05 to 5 wt. %, preferably about 0.05 to 2 wt. %, and more preferably about 0.05 to 1 wt. %. Low carbon monoxide production is desirable in combination with higher hydrogen combinations in some embodiments.

The particularly desirable combination of products in the reactor effluent is provided by selection of reaction conditions for use in combination with the molecular sieve and Group 2-14 element. Thus, in particular embodiments, the reactor 103 is operated at a weight hourly space velocity (WHSV) in the range of from 0.1 to 60 $hr^{-1}$, preferably 0.50 to 12.0 $hr^{-1}$, more preferably 0.5 to 5 $hr^{-1}$, and most preferably 0.5 to 2 $hr^{-1}$.

Additionally or alternatively, the first mixture comprising the oxygenate is exposed in reactor 103 to a temperature ≥350° C., preferably about 350 to 600° C., more preferably about 400 to 600° C., and most preferably about 400 to 550° C., and a pressure ≥2 bar absolute, preferably about 2 to 100 bar absolute, more preferably about 4 to 50 bar absolute, and most preferably about 8 to 25 bar absolute. Ranges and combinations of temperatures and pressures expressly disclosed include combinations of any of the above-enumerated upper and lower limits.

The product stream from reactor 103 is provided via a line 104 to first separation unit 105 for separation into (i) at least one water-rich stream 106, (ii) at least one aromatic-rich hydrocarbon stream 107, and (iii) at least one aromatic-depleted hydrocarbon stream 108. First separation unit 105 may be any suitable separation means, e.g., distillation tower, simulated moving-bed separation unit, high pressure separator, low pressure separator, flash drum, etc. Optionally, at least a portion of aromatics-rich hydrocarbon stream 107 may be recycled to reactor 103 via recycle line 107a, e.g., by combination directly or indirectly with the first mixture in line 101, prior to or after the optional dehydration unit 102. In particular embodiments, wherein ≥50.0 wt. %, 50.0 to 100 wt. %, 60.0 to 95.0 wt. %, 70.0 to 90.0 wt. %, 80.0 to 85.0 wt. %, of the first mixture's aromatics are the recycled aromatics, weight percents being based on the total amount of aromatics in the first mixture.

Optionally, at least a portion of aromatic-depleted hydrocarbon stream 108 exiting first separation unit 105 may be recycled to reactor 103, e.g., by combination, directly or indirectly, with line 101. In another embodiment, oxygenates in aromatics-depleted hydrocarbon stream 108 may be recovered therefrom. At least a portion of the recovered oxygenates may thereafter be provided to reactor 103. Additionally or alternatively, at least one of ethylene, propylene, and butylenes may be recovered from at least a portion of the aromatics-depleted hydrocarbon stream 108.

Figure 2:
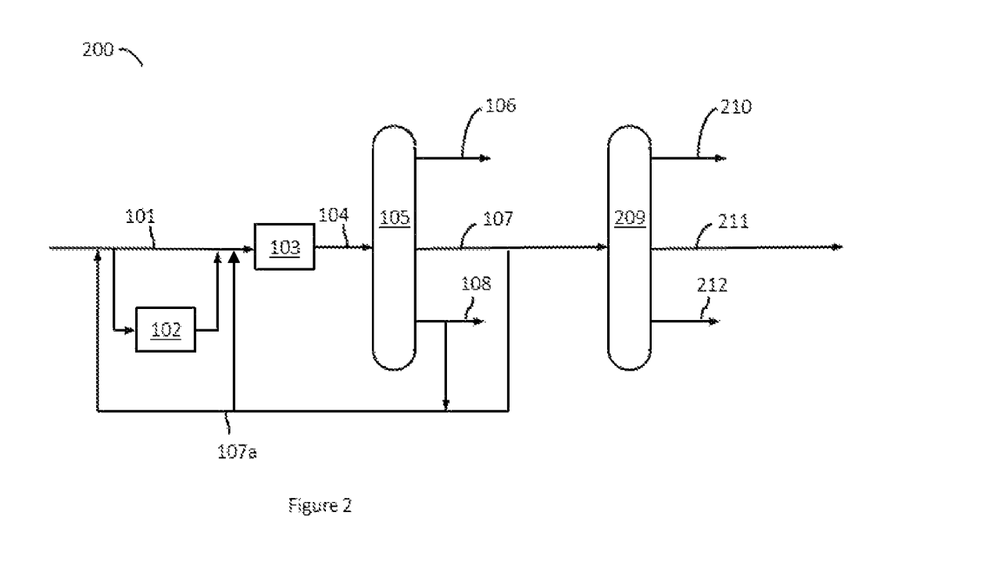
FIG. 2 illustrates a process according to an embodiment of the invention wherein an aromatic-rich hydrocarbon stream is separated into first, second and third streams.

With continuing reference to FIG. 1, FIG. 2 schematically depicts a process 200 according to particular embodiments. The aromatic-rich hydrocarbon stream 107 is provided to a second separation unit 209 configured to separate the aromatic-rich stream into (i) at least one first stream 210 comprising oxygenate and $C_6$ and/or $C_7$ aromatics, (ii) at least one second stream 211 comprising oxygenate and $C_8$ aromatics, and (iii) at least one third stream 212 comprising oxygenate and $C_{9+}$ aromatics. Second separation unit 209 may be any device or process suitable for performing such a separation, e.g., distillation tower, simulated moving-bed separation unit, high pressure separator, low pressure separator, flash drum, etc.

Figure 3:
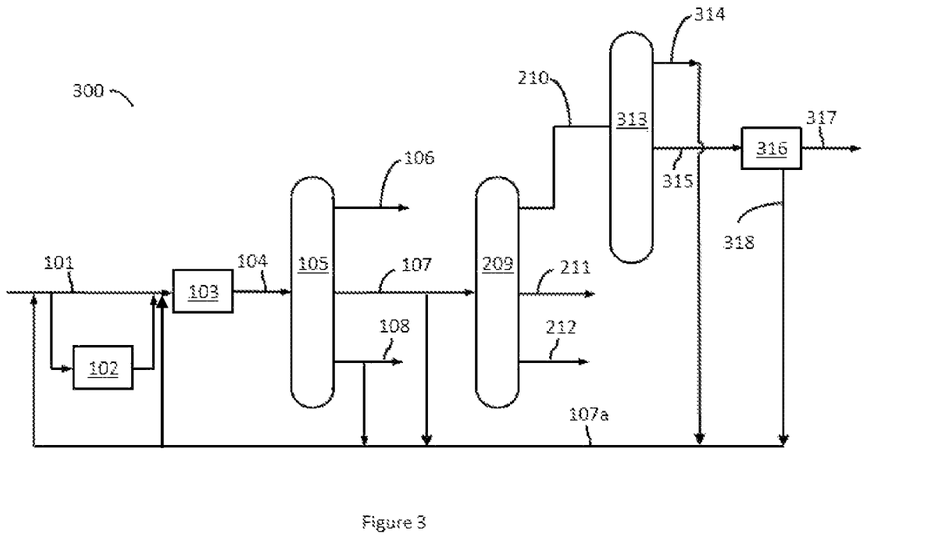
FIG. 3 illustrates a process according to an embodiment of the invention wherein the first stream is separated into a first oxygenate stream and a second aromatics-rich stream comprising $C_6$ and/or $C_7$ aromatics.
Figure 4:
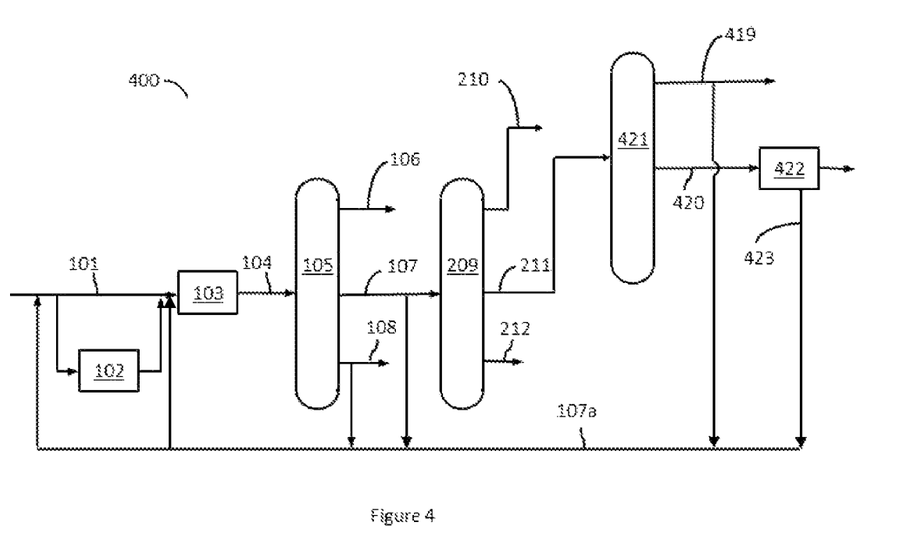
FIG. 4 illustrates a process according to an embodiment of the invention wherein the second stream is separated into a second oxygenate stream and a third aromatics-rich stream.
Figure 5:
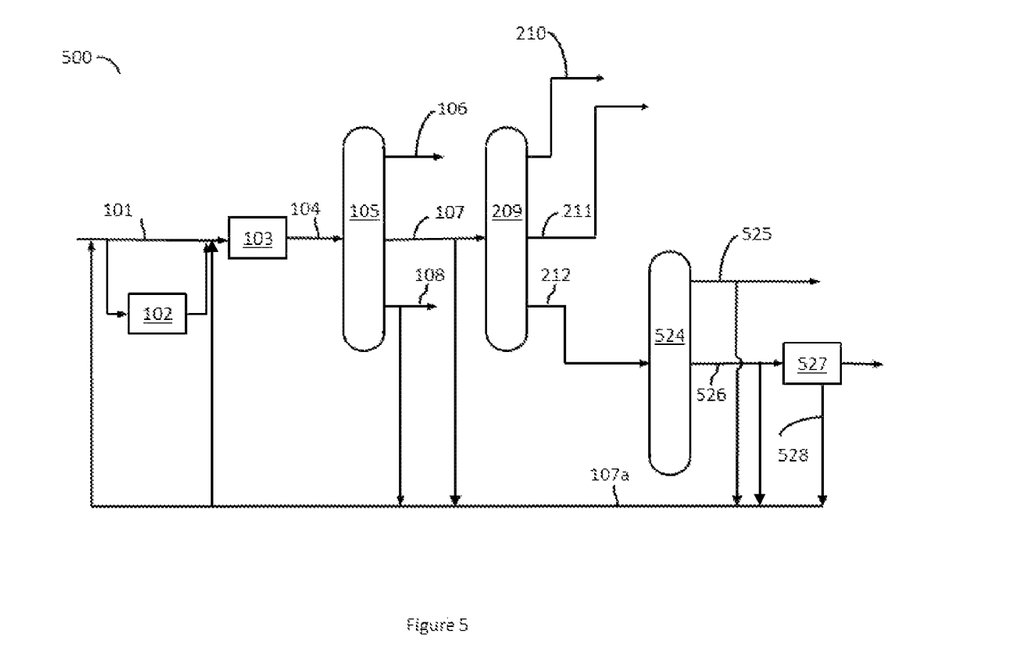
FIG. 5 illustrates a process according to an embodiment of the invention wherein the third stream is separated into a third oxygenate stream and a fourth aromatics-rich stream comprising $C_{9+}$ aromatics.
Figure 6:
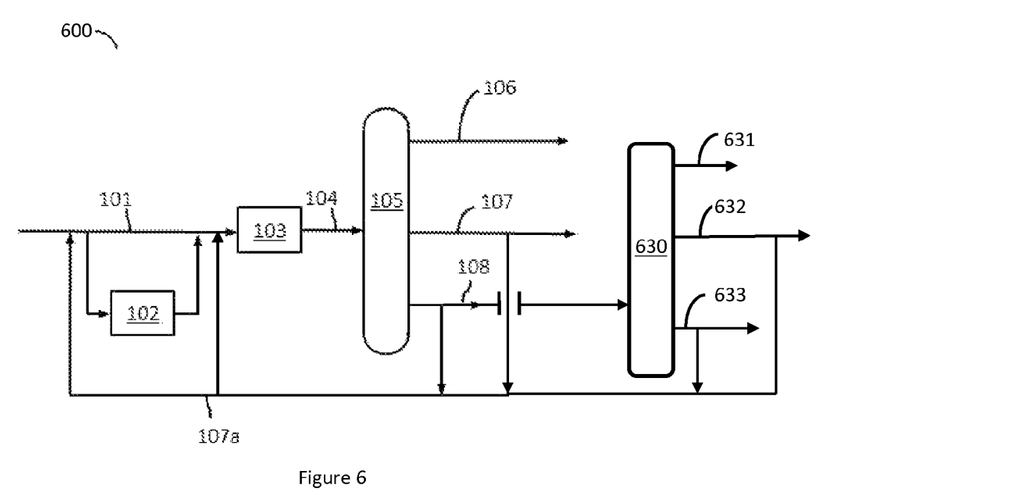
FIG. 6 illustrates a process according to an embodiment of the invention wherein an aromatic-depleted hydrocarbon stream is separated into a paraffin-rich stream and an olefin-rich stream.

With continuing reference to FIGS. 1 and 2, FIG. 3 schematically depicts a process 300 according to particular embodiments. Optionally, the first stream 210 may be provided to a third separation unit 313 configured to separate from the first stream 210 a first oxygenate stream 314 and a second aromatics-rich stream 315, the aromatics-rich stream 315 comprising $C_6$ and/or $C_7$ aromatics. Optionally, at least a portion of first oxygenate stream 314 may be recycled to reactor 103, e.g., by combining with the first mixture in line 101, e.g., via line 107a, prior to or after the optional dehydration unit 102. Third separation unit 313 may be any separation unit suitable for such a separation, e.g., distillation tower, simulated moving-bed separation unit, high pressure separator, low pressure separator, flash drum, etc. In particular embodiments, the second aromatics-rich stream 315 is provided to a recovery unit 316 for recovering benzene and or toluene therefrom via line 317. At least a portion of residual fraction 318 exiting recovery unit 316 may be combined with the first mixture and provided to the reactor 103 via line 101, e.g., via recovery line 107a, prior to or after the optional dehydration unit 102. Optionally, at least a portion of the second aromatics-rich stream 315, benzene, or toluene 317 is provided to a toluene alkylation, toluene disproportionation or transalkylation unit to produce xylenes (not shown in FIG. 3). Toluene alkylation is described in more detail in, for example, U.S. Pat. Nos. 6,423,879; 6,642,426; 6,388,156; 7,799,962; 8,048,388; 8,399,727; and 8,344,197. Toluene disproportionation is described in more detail in, for example, U.S. Pat. Nos. 5,993,642; 6,039,864; 6,198,013; and 6,486,373. Transalkylation is described in more detail in, for example, U.S. Pat. Nos. 7,553,791; 8,071,828; 8,183,424; and 8,481,443.

With continuing reference to FIGS. 1-3, FIG. 4 schematically depicts a process 400 according to particular embodiments. Such embodiments, which may optionally include the separation scheme of process 300, include separating from the second stream 211 a second oxygenate stream 419 and a third aromatics-rich stream 420 in a fourth separation unit 421. Fourth separation unit 421 may be any device or process suitable for performing such a separation, e.g. distillation tower, simulated moving-bed separation unit, high pressure separator, low pressure separator, flash drum, etc. Optionally, at least a portion of second oxygenate stream 419 may be recycled to reactor 103, e.g., by combining directly or indirectly with the first mixture in line 101, e.g., via recycle line 107a, prior to or after the optional dehydration unit 102. Typically, the third aromatics-rich stream 420 comprises $C_{8+}$ aromatics. Third aromatics-rich stream 420 may be provided to a second recovery unit 422 for recovering para-xylene therefrom. At least a portion of residual fraction 423 exiting recovery unit 422 may be combined with the first mixture and provided to the reactor 103 via line 101, e.g., via recycle line 107a, prior to or after the optional dehydration unit 102. Optionally, at least a portion of the para-xylene depleted residual fraction 423 may be sent to a xylenes isomerization unit to produce a mixed xylenes stream from which para-xylene may be recovered.

With continuing reference to FIGS. 1-4, FIG. 5 schematically depicts a process 500 according to particular embodiments. Process 500 may, additionally or alternatively, include separating third stream 212 by any suitable means 524 into a third oxygenate stream 525 and a fourth aromatics-rich stream 526, the fourth aromatics-rich stream comprising $C_{9+}$ aromatics. Fourth aromatics stream 526 may optionally be provided to a transalkylation unit 527 to transalkylate at least a portion of the fourth aromatics-rich stream to produce xylenes. Optionally, at least a portion of third oxygenate stream 525, the fourth aromatics stream 526, and/or at least a portion of residual fraction 528 exiting transalkylation unit 527 may be recycled, directly or indirectly, to reactor 103, e.g., by combining with the first mixture in line 101 via recycle line 107a, prior to or after the optional dehydration unit 102.

It has also been found that recycling and combining at least a portion of the aromatics in the hydrocarbon product with the oxygenate unexpectedly leads to one or more of the following advantages. In particular embodiments, recycling and combining at least a portion of the aromatics in the hydrocarbon product provides an increase in the relative amount of aromatics in the hydrocarbon product. The increase in aromatics may be achieved without a significant increase in the rate of catalyst deactivation and/or without a significant increase in the relative amount of durene in the aromatic portion of the hydrocarbon product. Advantageously and contrary to expectations, recycling and combining with the oxygenate at least a portion of the aromatics in the hydrocarbon product does not suppress methanol conversion to aromatic products. Under particular conditions, recycling of the aromatics can actually provide an overall increase in product aromatics content. Surprisingly, the catalyst may not experience a significant increase in deactivation rate, e.g., from over-reacting the recycled aromatics, even at elevated reaction temperatures (e.g., end of run conditions). And under certain conditions, the relative amount of durene in the aromatic portion of the product may not increase, even though recycling of xylenes to a chemical environment rich in CH2 fragments would be expected to result in alkylation to $C_{9+}$ aromatics. Specifically, recycling a portion or the complete stream of $C_{9+}$ aromatics at the reactor inter-stage facilitates heavy aromatics transalkylation that increases the relative amount of p-xylene in the hydrocarbon product.

With continuing reference to FIGS. 1-5, FIG. 6 schematically depicts a process 600 according to particular embodiments. Process 600 may, additionally or alternatively, include separating aromatics-depleted hydrocarbon stream 108 by any suitable means 631 into a fourth oxygenate stream 631, a paraffin-rich stream 632, and a olefins-rich stream 633. Optionally, at least a portion of the paraffin-rich stream 632 and/or the olefins-rich stream 633 may be recycled to reactor 103, e.g., by combining directly or indirectly with the first mixture in line 101, e.g., via recycle line 107a, prior to or after the optional dehydration unit 102.

It has also been found that recycling and combining at least a portion of the olefins or paraffins in the hydrocarbon product with the oxygenate unexpectedly leads to one or more of the following advantages. In particular embodiments, recycling and combining at least a portion of the olefins or paraffins in the hydrocarbon product provides an increase in the amount of aromatics in the hydrocarbon product. The increase in aromatics may be achieved without a significant increase in the rate of catalyst deactivation and/or without a significant increase in the relative amount of durene in the aromatic portion of the hydrocarbon product. Advantageously, recycling and combining with the oxygenate at least a portion of the olefins or paraffins leads to further conversion of the olefins and paraffins to aromatics without causing a significant increase in catalyst deactivation.

In one embodiment, in which either a portion of an aromatic-rich hydrocarbon stream, paraffin-rich stream, or olefin-rich stream is recycled to reactor 103, the recycled stream is independently fed to the reactor 103 at an independent WHSV than the first mixture. The weight hourly space velocity (WHSV) of the recycle stream may be in the range of from about 0.1 to 60 $hr^{-1}$, preferably about 0.50 to 12.0 $hr^{-1}$, more preferably about 0.5 to 5 $hr^{-1}$, and most preferably about 0.5 to 2 $hr^{-1}$.

The description and examples above support one or more of the following more specific Embodiments.

Embodiment 1

An aromatic production process, comprising: (a) providing a first mixture comprising ≥10.0 wt. % of at least one oxygenate, based on the weight of the first mixture, to a fluidized or moving bed reactor; (b) contacting said first mixture with a catalyst in said reactor at a temperature of 350.0 to 700.0° C. to convert said first mixture to a product stream comprising water, one or more hydrocarbons, hydrogen, and one or more oxygenates, wherein (1) said catalyst comprises at least one molecular sieve, at least one element selected from Groups 2-14 of the Periodic Table, and a binder, (2) said one or more hydrocarbons comprise ≥30.0 wt. % of aromatics, based on the weight of said one or more hydrocarbons in the product stream; (c) separating from said product stream (i) at least one water-rich stream, (ii) at least one aromatic-rich hydrocarbon stream, and (iii) at least one aromatic-depleted hydrocarbon stream; and (d) recycling at least a portion of one of the (i) at least one aromatic-rich hydrocarbon stream or (ii) at least one aromatic-depleted hydrocarbon stream to said reactor to contact the catalyst in step (b).

Embodiment 2

The process of Embodiment 1, wherein the first mixture comprises ≥90.0 wt. % of methanol and/or dimethylether and wherein the process further comprises separating from the aromatic-rich hydrocarbon stream (i) at least one first stream comprising oxygenate and $C_6$ and/or $C_7$ aromatics, (ii) at least one second stream comprising oxygenate and $C_8$ aromatics, and (iii) at least one third stream comprising oxygenate and $C_{9+}$ aromatics.

Embodiment 3

The process of Embodiment 2, further comprising recycling at least a portion of the first stream to said reactor to contact the catalyst in step (b).

Embodiment 4

The process of Embodiment 2, further comprising separating from the first stream a first oxygenate stream and a second aromatics-rich stream, the second aromatics-rich stream comprising $C_6$ and/or $C_7$ aromatics.

Embodiment 5

The process of Embodiment 4, further comprising recovering benzene and/or toluene from the second aromatics-rich stream.

Embodiment 6

The process of Embodiment 4 or 5, further comprising sending at least a portion of the second aromatics-rich stream to a toluene alkylation, toluene disproportionation or transalkylation unit to produce xylenes.

Embodiment 7

The process of Embodiment 2, further comprising separating from the second stream a second oxygenate stream and a third aromatics-rich stream, the third aromatics-rich stream comprising $C_{8+}$ aromatics.

Embodiment 8

The process of Embodiment 7, further comprising recovering para-xylene and a para-xylene depleted stream from the third aromatics-rich stream.

Embodiment 9

The process of Embodiment 8, further comprising sending at least a portion of para-xylene depleted stream to a xylenes isomerization unit to produce a mixed xylenes stream and recovering para-xylene from the mixed xylenes stream.

Embodiment 10

The process of Embodiment 2, further comprising separating from the third stream a third oxygenate stream and a fourth aromatics-rich stream, the fourth aromatics-rich stream comprising $C_{9+}$ aromatics.

Embodiment 11

The process of Embodiment 11, further comprising transalkylating at least a portion of the fourth aromatics-rich stream to produce xylenes.

Embodiment 12

The process of claim 10, further comprising recycling at least a portion of the fourth aromatics-rich stream to said reactor to contact the catalyst in step (b).

Embodiment 13

The process of any one of Embodiments 1-12, further comprising separating from the aromatic-depleted hydrocarbon stream (i) at least one fourth stream comprising oxygenate stream, (ii) at least one paraffin-rich stream, and (iii) at least one olefin-rich stream.

Embodiment 14

The process of claim 13, comprising recycling at least a portion of the paraffin-rich stream to said reactor to contact the catalyst in step (b).

Embodiment 15

The process of claim 13, comprising recycling at least a portion of the olefin-rich stream to said reactor to contact the catalyst in step (b).

Embodiment 16

The process of Embodiment 4, 7, 10, or 14, further comprising contacting at least a portion of the first, the second, the third, or the fourth oxygenate streams with the catalyst in step (b).

Embodiment 17

An oxygenate conversion process, the process comprising: (a) providing a first mixture, the first mixture comprising ≥10.0 wt. % oxygenate based on the weight of the first mixture, to a fluidized or moving bed reactor; (b) exposing the first mixture at a temperature ≥400° C. at a pressure ≥2 bar absolute in the presence of a catalyst to convert ≥90.0 wt. % of the first mixture's oxygenate to (i) water, (ii) hydrocarbon, and (iii) ≤1.0 wt. % carbon monoxide, the weight percents being based on the weight of oxygenate in the first mixture, wherein (1) the catalyst comprises ≥10.0 wt. % of at least one molecular sieve, ≥0.1 wt. % of at least one element selected from Groups 2-14 of the Periodic Table and about 1.0 to 90.0 wt. % of a binder, the weight percents being based on the weight of the catalyst, and (2) the hydrocarbon comprises ≥50.0 wt. % of aromatics, based on the weight of the hydrocarbon; and (c) separating the aromatics from one or more of (i) at least a portion of the water produced in step (b), (ii) any unreacted oxygenate, and/or (iii) at least a portion of the hydrocarbon.

Embodiment 18

The process of Embodiment 17, wherein (i) the first mixture comprises ≥25.0 wt. % oxygenate, based on the weight of the first mixture, and (ii) the oxygenate comprises ≥90.0 wt. % based on the weight of the oxygenate of one or more of alcohol, ether, carboxylic acid, carbon monoxide, or carbon dioxide.

Embodiment 19

The process of Embodiment 18, wherein the oxygenate comprises ≥99.0 wt. % of methanol and/or dimethylether.

Embodiment 20

The process of Embodiment 20, wherein the oxygenate comprises ≥99.0 wt. % of methanol, the exposing of step (b) is conducted at a weight hourly space velocity in the range of from 0.5 to 12 hr-1, the hydrocarbon comprises ≥80.0 wt. % of aromatics, based on the weight of the hydrocarbon, and ≤30.0 wt. % of the aromatics comprise durene, based on the weight of the aromatics.

Embodiment 21

The process of any one of Embodiments 17-20, wherein the first mixture further comprises ≥10.0 wt. % aromatics, based on the weight of the first mixture.

Embodiment 22

The process of any one of Embodiments 17-21, further comprising recycling at least a portion of the separated aromatics from step (c) to step (a), wherein ≥50.0 wt. % of the first mixture's aromatics are the recycled aromatics.

Embodiment 23

The process of any one of Embodiments 17-22, further comprising separating paraffins from the hydrocarbons in step (c) and recycling at least a portion of the separated paraffins, wherein the first mixture comprises ≥10.0 wt. % paraffins, based on the weight of the first mixture.

Embodiment 24

The process of any one of Embodiments 17-23, further comprising separating olefins from the hydrocarbons in step (c) and recycling at least a portion of the separated olefins, wherein the first mixture comprises ≥10.0 wt. % olefins, based on the weight of the first mixture.

Embodiment 25

The process of any one of Embodiments 1-24, wherein the molecular sieve comprises ZSM-5, the element comprises Zn, and a binder selected from the group consisting of silica-alumina, silica-magnesia, silica-zirconia, silica-thoria, silica-beryllia, silica-titania, silica-alumina-thoria, silica-alumina-zirconia, silica-alumina-magnesia and silica-magnesia-zirconia.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the enforceable scope of the present invention.

All documents described herein are incorporated by reference for purposes of all jurisdictions where such practice is allowed, including any priority documents and/or testing procedures to the extent they are not inconsistent with this text, provided however, that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. An aromatic production process, comprising:
   (a) providing a first mixture comprising ≥10.0 wt. % of at least one oxygenate, based on the weight of the first mixture, to a fluidized or moving bed reactor;
   (b) contacting the first mixture with a catalyst in the reactor at a temperature of 350.0 to 700.0° C. to convert the first mixture to a product stream comprising water, one or more hydrocarbons, hydrogen, and one or more oxygenates, wherein:
      (1) the catalyst comprises at least one molecular sieve, at least one element selected from Groups 2-14 of the Periodic Table, and a binder; and
      (2) the one or more hydrocarbons comprise ≥30.0 wt. % of aromatics, based on the weight of the one or more hydrocarbons in the product stream;
   (c) separating from said product stream (i) at least one water-rich stream, (ii) at least one aromatic-rich hydrocarbon stream, and (iii) at least one aromatic-depleted hydrocarbon stream;
   (d) recycling at least a portion of one of the (i) at least one aromatic-rich hydrocarbon stream or (ii) at least one aromatic-depleted hydrocarbon stream to said reactor to contact the catalyst in step (b);
   (e) separating from the aromatic-rich hydrocarbon stream (i) a first stream comprising oxygenate and $C_6$ and/or $C_7$ aromatics, (ii) a second stream comprising oxygenate and $C_8$ aromatics, and (iii) a third stream comprising oxygenate and $C_{9+}$ aromatics; and
   (f) separating an oxygenate stream from at least one of the first stream, the second stream, or the third stream.

2. The process of claim 1, wherein the first mixture comprises ≥90.0 wt. % of methanol and/or dimethylether.

3. The process of claim 2, further comprising recycling at least a portion of the first stream to said reactor to contact the catalyst in step (b).

4. The process of claim 2, wherein the separating in (f) comprises separating from the first stream a first oxygenate stream and a second aromatics-rich stream, the second aromatics-rich stream comprising $C_6$ and/or $C_7$ aromatics.

5. The process of claim 4, further comprising recovering benzene and/or toluene from the second aromatics-rich stream.

6. The process of claim 4, further comprising sending at least a portion of the second aromatics-rich stream to a toluene alkylation, toluene disproportionation or transalkylation unit to produce xylenes.

7. The process of claim 4, further comprising recycling at least a portion of the first oxygenate stream to said reactor to contact the catalyst in step (b).

8. The process of claim 2, wherein the separating in (f) comprises separating from the second stream a second oxygenate stream and a third aromatics-rich stream, the third aromatics-rich stream comprising $C_{8+}$ aromatics.

9. The process of claim 7, further comprising recovering para-xylene and a para-xylene depleted stream from the third aromatics-rich stream.

10. The process of claim 8, further comprising sending at least a portion of the para-xylene depleted stream to a xylenes isomerization unit to produce a mixed xylenes stream and recovering para-xylene from the mixed xylenes stream.

11. The process of claim 2, wherein the separating in (f) comprises separating from the third stream a third oxygenate stream and a fourth aromatics-rich stream, the fourth aromatics-rich stream comprising $C_{9+}$ aromatics.

12. The process of claim 11, further comprising transalkylating at least a portion of the fourth aromatics-rich stream to produce xylenes.

13. The process of claim 11, further comprising recycling at least a portion of the fourth aromatics-rich stream to said reactor to contact the catalyst in step (b).

14. The process of claim 1, further comprising separating from the aromatic-depleted hydrocarbon stream (i) at least one fourth oxygenate stream, (ii) at least one paraffin-rich stream, and (iii) at least one olefin-rich stream.

15. The process of claim 14, comprising recycling at least a portion of the paraffin-rich stream to said reactor to contact the catalyst in step (b).

16. The process of claim 14, comprising recycling at least a portion of the olefin-rich stream to said reactor to contact the catalyst in step (b).

17. The process of claim 1, wherein the molecular sieve comprises ZSM-5, the element comprises Zn, and a binder selected from the group consisting of silica-alumina, silica-magnesia, silica-zirconia, silica-thoria, silica-beryllia, silica-titania, silica-alumina-thoria, silica-alumina-zirconia, silica-alumina-magnesia and silica-magnesia-zirconia.

18. An oxygenate conversion process, the process comprising:
   (a) providing a first mixture, the first mixture comprising ≥10.0 wt. % oxygenate based on the weight of the first mixture, to a fluidized or moving bed reactor;
   (b) contacting the first mixture with a catalyst at a temperature ≥400° C. and a pressure ≥2 bar absolute to convert ≥90.0 wt. % of the first mixture's oxygenate to (i) water, (ii) hydrocarbon, and (iii) ≤1.0 wt. % carbon monoxide, the weight percents being based on the weight of oxygenate in the first mixture, wherein:
      (1) the catalyst comprises ≥10.0 wt. % of at least one molecular sieve, ≥0.1 wt. % of at least one element selected from Groups 2-14 of the Periodic Table and about 1.0 to 90.0 wt. % of a binder, the weight percents being based on the weight of the catalyst, and
      (2) the hydrocarbon comprises ≥50.0 wt. % of aromatics, based on the weight of the hydrocarbon; and
   (c) separating from the hydrocarbon (i) an aromatic-rich hydrocarbon stream, and (ii) an aromatic-depleted hydrocarbon stream;
   (d) separating paraffins and/or olefins from the aromatic-depleted hydrocarbon stream and recycling at least a portion of the separated paraffins and/or olefins to the reactor to contact the catalyst in step (b);
   (e) separating from the aromatic-rich hydrocarbon stream (i) a first stream comprising $C_6$ and/or $C_7$ aromatics, (ii) a second stream comprising $C_8$ aromatics, and (iii) a third stream comprising $C_{9+}$ aromatics; and (f) separating an oxygenate stream from at least one of the first stream, the second stream, or the third stream.

19. The process of claim 18, wherein (i) the first mixture comprises ≥25.0 wt. % oxygenate, based on the weight of the first mixture, and (ii) the oxygenate in the first mixture comprises ≥90.0 wt. % based on the weight of the oxygenate of one or more of alcohol, ether, carboxylic acid, carbon monoxide, or carbon dioxide.

20. The process of claim 19, wherein the oxygenate in the first mixture comprises ≥99.0 wt. % of methanol and/or dimethylether.

21. The process of claim 19, wherein the oxygenate in the first mixture comprises ≥99.0 wt. % of methanol, the contacting of step (b) is conducted at a weight hourly space velocity in the range of from 0.5 to 12 $hr^{-1}$, the hydrocarbon comprises ≥80.0 wt. % of aromatics, based on the weight of the hydrocarbon, and ≤30.0 wt. % of the aromatics comprise durene, based on the weight of the aromatics.

22. The process of claim 18, wherein the first mixture further comprises ≥10.0 wt. % aromatics, based on the weight of the first mixture.

23. The process of claim 18, further comprising recycling aromatics from the aromatics-rich hydrocarbon stream to step (a), wherein ≥50.0 wt. % of the first mixture's aromatics are the recycled aromatics.

24. The process of claim 18, wherein the first mixture comprises ≥10.0 wt. % paraffins, based on the weight of the first mixture.

25. The process of claim 18, wherein the first mixture comprises ≥10.0 wt. % olefins, based on the weight of the first mixture.

26. The process of claim 18, wherein the molecular sieve comprises ZSM-5, the element comprises Zn, and a binder selected from the group consisting of silica-alumina, silica-magnesia, silica-zirconia, silica-thoria, silica-beryllia, silica-titania, silica-alumina-thoria, silica-alumina-zirconia, silica-alumina-magnesia and silica-magnesia-zirconia.

* * * * *